(12) United States Patent
Dayal et al.

(10) Patent No.: US 7,046,352 B1
(45) Date of Patent: May 16, 2006

(54) SURFACE INSPECTION SYSTEM AND METHOD USING SUMMED LIGHT ANALYSIS OF AN INSPECTION SURFACE

(75) Inventors: Aditya Dayal, Sunnyvale, CA (US); David S. Alles, Los Altos, CA (US); George Q. Chen, Fremont, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 400 days.

(21) Appl. No.: 10/325,023

(22) Filed: Dec. 19, 2002

Related U.S. Application Data (60) Provisional application No. 60/417,231, filed on Oct. 8, 2002.

(51) Int. Cl.
*G01N 21/00* (2006.01)
(52) U.S. Cl. ............... 356/237.1; 356/237.2; 356/237.4; 356/237.5
(58) Field of Classification Search .. 356/237.1–237.5, 356/241.1–241.6, 238.1–238.3, 239.1–239.8, 356/240.1; 250/559.4–559.45; 382/141, 382/145, 148, 149; 348/126, 128, 125
See application file for complete search history.

(56) References Cited

U.S. PATENT DOCUMENTS

| | | | | |
|---|---|---|---|---|
| 4,247,203 A | | 1/1981 | Levy et al. | 356/398 |
| 4,555,798 A | * | 11/1985 | Broadbent et al. | 382/144 |
| 4,669,885 A | * | 6/1987 | Ina | 356/443 |
| 5,204,910 A | * | 4/1993 | Lebeau | 382/152 |
| 5,327,286 A | * | 7/1994 | Sampsell et al. | 359/561 |
| 5,563,702 A | | 10/1996 | Emery et al. | 356/73 |
| 6,268,093 B1 | * | 7/2001 | Kenan et al. | 430/30 |
| 6,466,315 B1 | * | 10/2002 | Karpol et al. | 356/237.4 |
| 6,727,987 B1 | * | 4/2004 | Yonezawa | 356/237.2 |

OTHER PUBLICATIONS

Burn J. Lin, "Phase-Shifting and Other Challenges in Optical Mask Technology", SPIE vol. 1496 10th Annual Symposium on Microlithography (1990), pp. 54-79.
J. R. Parker, "Algorithms for Image Processing and Computer Vision", John Wiley & Sons, Inc., ISBN 0-471-14056-2 (1997), pp. 70-71, 103-104.
Bruning et al., "An Automated Mask Inspection System—AMIS", IEEE Transactions on Electron Devices, vol. ED-22, No. 7, Jul. 1975, pp. 487-495.

* cited by examiner

*Primary Examiner*—Gregory J. Toatley, Jr.
*Assistant Examiner*—Gordon J. Stock, Jr.
(74) *Attorney, Agent, or Firm*—Beyer Weaver&Thomas,LLP (57) ABSTRACT

The present invention discloses methods of conducting surface inspections using summed light. One method includes the steps of measuring summed light intensity values for the substrate, generating comparison values for the substrate, and then comparing the measured summed light intensity values with the comparison values to determine whether there are defects in the substrate. In another embodiment, a method includes the steps of generating a reference cluster using measured summed light intensity values for selected portions of the inspection surface. Other summed light intensity values are measured and then compared with the reference cluster. Using this comparison, a determination is made as to whether a defect is present. Another embodiment uses a constant baseline signal which is compared to actual light intensity values to determine whether a substrate defect is present. In yet another embodiment a substrate is inspected for the presence of defects by conducting a pixel-by-pixel summed light inspection of the substrate.

18 Claims, 7 Drawing Sheets

SURFACE INSPECTION SYSTEM AND METHOD USING SUMMED LIGHT ANALYSIS OF AN INSPECTION SURFACE

RELATED APPLICATION

This application is related to, and claims priority from, U.S. Provisional Patent Application Ser. No. 60/417,231, entitled "Surface Inspection System and Method Using Summed Light Analysis Inspection Surface", by Dayal et al., filed on Oct. 8, 2002 which is hereby incorporated by reference in its entirety for all purposes.

TECHNICAL FIELD

The invention described herein relates generally to surface inspection and testing. In particular, the invention relates to systems and methods for summed light inspection of optical masks and reticles and the like.

BACKGROUND

Integrated circuit fabrication utilizes photolithographic processes which use photomasks or reticles and an associated light source to project circuit images onto silicon wafers. A high production yield is contingent on having defect-free masks and reticles. Since it is inevitable that defects will occur in the mask, these defects have to be found and repaired prior to using the mask.

Automated mask inspection systems have existed for over 20 years. The earliest such system, the Bell Telephone Laboratories AMIS system (John Bruning et al., "An Automated Mask Inspection System—AMIS", IEEE Transactions on Electron Devices, Vol. ED-22, No. 7 Jul. 1971, pp 487 to 495), used a laser that scanned the mask. Subsequent systems used a linear sensor to inspect an image projected by the mask, such as described by Levy et al. (U.S. Pat. No. 4,247,203, "Automatic Photomask Inspection System and Apparatus"). Such a technology teaches die-to-die inspection, i.e., inspection of two adjacent dice by comparing them to each other.

As the complexity of integrated circuits has increased, so have the demands on the inspection process. The needs for resolving smaller defects and for inspecting larger areas have resulted in much greater speed requirements, in terms of number of picture elements per second processed. Numerous improvements have been made in an attempt to keep pace with these increased demands.

Another force driving the development of improved inspection techniques is the emergence of phase shift mask technology. With this technology it will be possible to print finer line widths, down to 0.18 micrometers (µm) or less. Typical examples of this technology are described by Burn J. Lin, "Phase-Shifting and Other Challenges in Optical Mask Technology", Proceedings of the 10th Annual Symposium on Microlithography, SPIE, The International Society of Optical Engineering, Vol. 1496, pages 54 to 79.

Photomasks are used in the semiconductor manufacturing industry for the purpose of transferring photolithographic patterns onto a substrate such as silicon, gallium arsenide, or the like, during the manufacture of integrated circuits. The photomask is typically composed of a polished transparent substrate, such as a fused quartz plate, on which a thin patterned opaque layer, consisting of figures, has been deposited on one surface. Typically, the patterned opaque layer is chromium with a thickness of 800 to 1200 angstroms. This layer may have a light anti-reflection coating deposited on one or both surfaces of the chromium. In order to produce functioning integrated circuits at a high yield rate, the photomasks need to be free of defects. A defect is defined here as any unintended marring of the intended photolithographic pattern. Such defects can include particles, pits, bumps, scratches, and other like blemishes in an inspection surface. Such defects can be caused during the manufacture of the photomask or as a result of the use of the photomask. Defects can be due to, and not limited to, a portion of the opaque layer being absent from an area of the photolithographic pattern where it is intended to be present, a portion of the opaque layer being present in an area of the photolithographic pattern where it is not intended to be, chemical stains or residues from the photomask manufacturing processes which cause an unintended localized modification of the light transmission property of the photomask, particulate contaminates such as dust, resist flakes, skin flakes, erosion of the photolithographic pattern due to electrostatic discharge, artifacts in the photomask substrate such as pits, scratches, and striations, and localized light transmission errors in the substrate or opaque layer. During the manufacture of photomasks, automated inspection of the photomask is performed in order to ensure a freedom from the aforementioned defects.

Certain apparatuses have been constructed that separately measure either reflected or transmitted light and use both to classify defects. Both types of light are valuable for detecting different types of defects. However, such devices do not commonly detect light that is reflected and transmitted simultaneously from the same point on the inspection surface. In particular, such devices do not make use of detector arrays to capitalize on the advantages of such techniques. Additionally, such devices require the use of one or more discrete detector elements to individually and separately detect reflected light and transmitted light.

Embodiments of the present invention can be used to overcome these and other limitations of the existing art.

SUMMARY OF THE INVENTION

In accordance with the principles of the present invention, a method of conducting surface inspection using measurements of summed reflected and transmitted light is disclosed.

One embodiment of the invention is a surface inspection method for detecting defects in a substrate including the steps of measuring summed light intensity values for the substrate, generating comparison values for the substrate, and then comparing the measured summed light intensity values with the comparison values to determine whether there are defects in the substrate.

In another surface inspection embodiment, a method includes the steps of generating a reference cluster using measured summed light intensity values for the inspection surface. Other summed light intensity values are measured and then compared with the reference cluster. Using this comparison, a determination is made as to whether a defect is present.

Another method embodiment describes a method for inspecting a substrate having a pattern of opaque material with both edge and non-edge regions formed thereon. The method includes setting a baseline signal value for summed light intensity values for non-edge regions of the substrate, the baseline signal comprising the sum of light reflected by the substrate and light transmitted through the substrate. The substrate is illuminated and summed light intensity values are measured. The measured summed light intensity values are comparing the actual light intensity values with the baseline signal value to determine whether a substrate defect is present.

In yet another method embodiment, a substrate can be inspected for the presence of defects by illuminating the substrate pixel-by-pixel with light and measuring summed light intensity values for each inspected pixel and then determining whether a defect is present in the substrate by comparing said intensity values with values calculated using a database model of the substrate.

In another method embodiment, a substrate can be inspected for the presence of defects by illuminating reference blocks of the substrate and detecting summed light from the reference blocks to generate a reference signal. A plurality of such reference signals is used to generate a reference cluster. Sample portions of the substrate are inspected to generate sample data signals representative of the summed light received from the sample portions. The sample data signals are comparing with the reference cluster to locate defects.

These and other aspects of the present invention are described in greater detail in the detailed description of the drawings set forth herein below.

BRIEF DESCRIPTION OF THE DRAWINGS

The following detailed description will be more readily understood in conjunction with the accompanying drawings, in which.

It is to be understood that, in the drawings, like reference numerals designate like structural elements. Also, it is understood that the depictions in the Figures are not necessarily to scale.

DETAILED DESCRIPTION OF EMBODIMENTS OF THE INVENTION

The present invention has been particularly shown and described with respect to certain embodiments and specific features thereof. The embodiments set forth herein below are to be taken as illustrative rather than limiting. It should be readily apparent to those of ordinary skill in the art that various changes and modifications in form and detail may be made without departing from the spirit and scope of the invention.

The following detailed description describes various embodiments of inspection tools and methods for their use. In particular, embodiments of the present invention are directed to methodologies for inspecting optical masks and reticles for the presence of unwanted defects. In most general terms, embodiments of the invention illuminate an inspection surface to create both reflected and transmitted light beams that are incident upon, or pass through, an inspection surface. The reflected light beams and transmitted light beams are detected by a photodetector array. In such a configuration, no distinction is made between the reflected light beams and transmitted light beams. Thus, the detector is said to measure summed light because the detector measures the total light intensity from both the reflected light beams and transmitted light beams. In other implementations, the reflected light beams and transmitted light beams can be detected separately.

Figure 1:
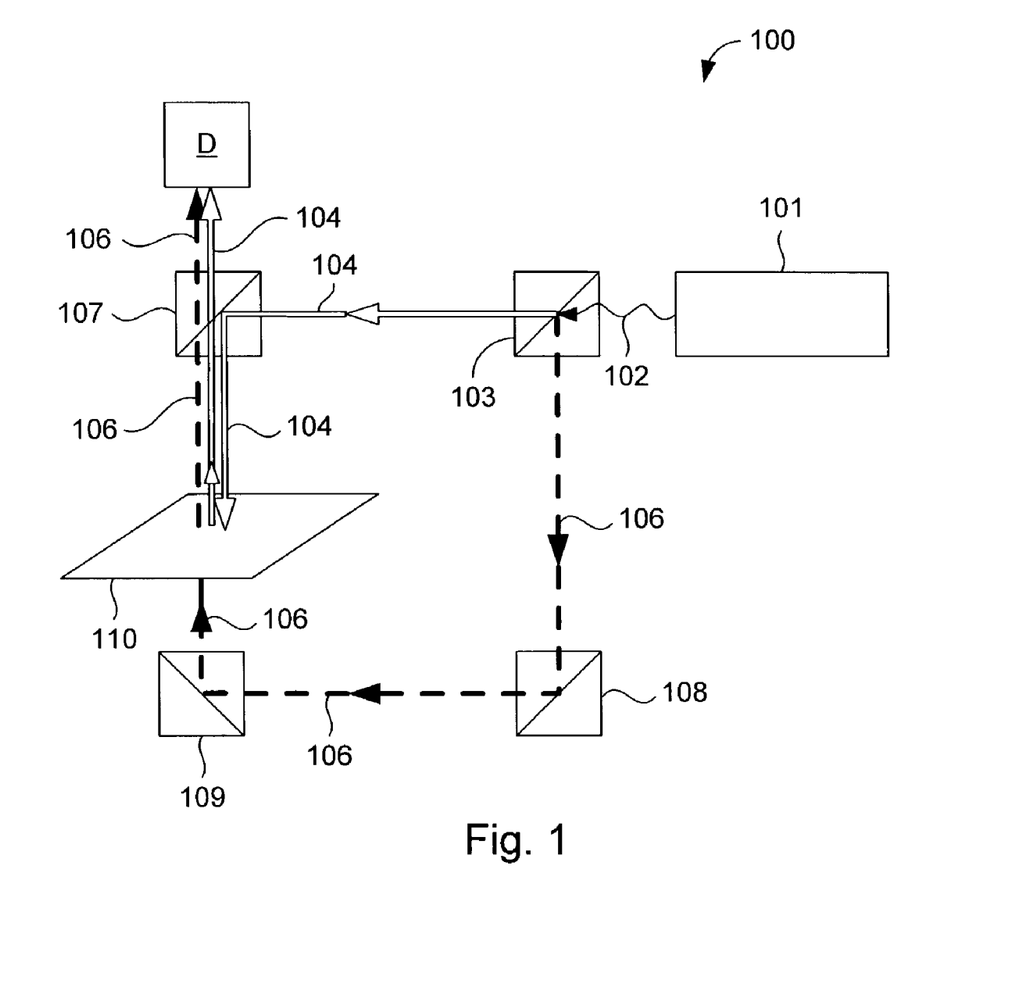
FIG. 1 is a schematic illustration of showing an apparatus embodiment capable of practicing method embodiments of the present invention.

An embodiment of a suitable apparatus capable of implementing the methodologies described herein is depicted in FIG. 1. FIG. 1 is a schematic diagram, which for simplicities sake, is depicted with many commonly used components omitted. Typical of such omitted components are optical elements such as lenses and electronics such as signal processing elements. The application of such components to the depicted embodiments is well known to persons having ordinary skill in the art. The depicted apparatus 100 includes a light source 101 for creating a suitable illumination beam 102. In this depiction, the light source 101 is a deep ultra-violet (DUV) laser capable of producing an illumination beam 102 having a wavelength of 257 nanometers (nm). Many other light sources and wavelengths can be used in accordance with the principles of the present invention. The illumination beam 102 is directed into a first beam splitter 103 that splits the illumination beam 102 into a "reflected" beam 104 and a "transmitted" beam 106.

The "reflected" beam 104 is defined as a light beam that will be directed onto, and reflected from, the "top" of the inspection surface 110 and is depicted here as a double-lined arrow. The reflected beam 104 exits the first beam splitter 103 and is then reflected by a second beam splitter 107 which directs a portion of the reflected beam 104 onto the top of the inspection surface 110. The top of the inspection surface 110 reflects a portion of the reflected beam 104. This light is reflected back through the second beam splitter 107 onto a photodetector element D. The photodetector element D can comprise a number of optical detectors including, but not limited to, photo arrays, imagers, photodiodes, and a host of related devices well known to persons having ordinary skill in the art. Many detector devices including charge-coupled device (CCD) detectors, time delay integration (TDI) detectors, and CMOS detectors can be used. In one embodiment, a TDI detector available from Hamamatsu of Japan can be used. Simultaneously, a "transmitted" beam 106 is also detected by the photodetector element D.

The "transmitted" beam 106 is defined as a light beam that is directed onto the bottom of the inspection surface 110 and passes therethrough. In this depiction, the transmitted beam 106 is indicated by the double dashed lined arrows. As explained above, the transmitted beam 106 is reflected by the first beam splitter 103 onto a first reflector 108 and a second reflector 109 which directs the transmitted beam 106 through the inspection surface 110. A portion of the light from this transmitted beam 106 passes through the second beam splitter 107 onto the photodetector element D where it is detected at the same time as the reflected beam 104. It is in this way that a pair of coaxial light beams (one transmitted 106, one reflected 104) pass through (or reflect from) the same point on the inspection surface 110 and then impinge on, and are detected by, the single detector element D. One example of a suitable apparatus is a 5XX-DUV Mask Inspection Tool available from KLA-Tencor Corporation of San Jose, Calif.

Figure 2A:
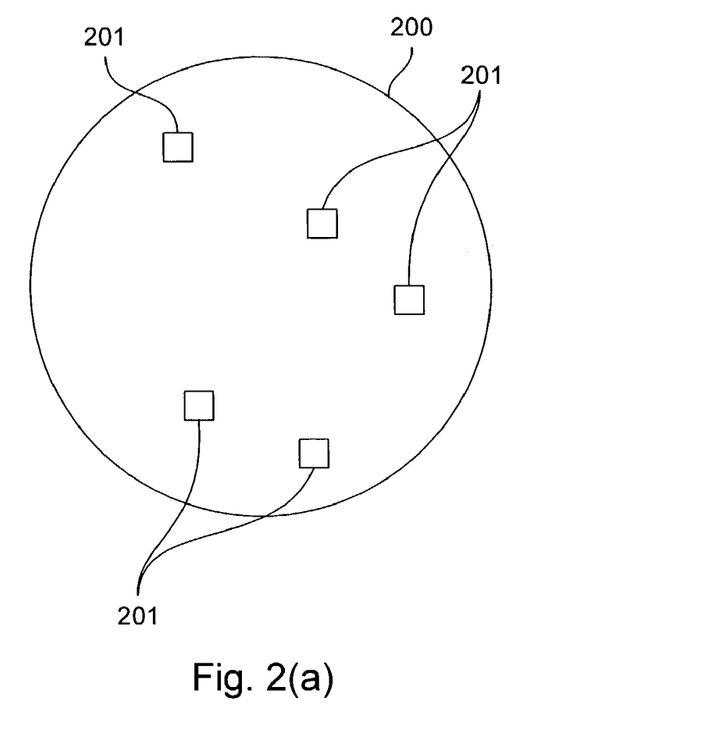
FIG. 2(a) is a plan view of a mask surface showing selected reference blocks.

In accordance with the principles of the present invention, such an apparatus can be used to detect defects in a mask (or other inspected surfaces). FIG. 2(a) is a schematic top down view of a typical mask 200 that can be inspected in accordance with the invention. Portions of the mask 200 can be defined as reference "blocks" 201. A plurality reference "blocks" 201 are depicted on this mask 200. The depicted reference blocks 201 are square portions of the mask surface. As is understood by persons having ordinary skill in the art, these reference blocks may assume a variety of other shapes and a variety of sizes.

Figure 2B:
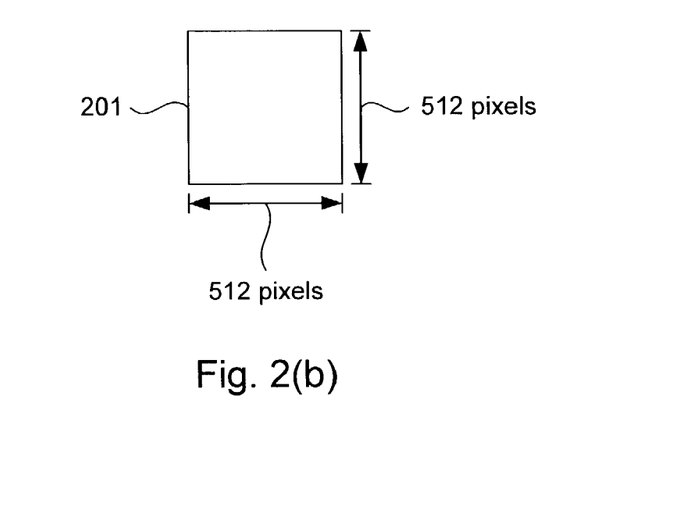
FIG. 2(b) is a depiction of an example reference block.

FIG. 2(b) is a close-up view of one embodiment of a reference block 201. The depicted reference block 201 is shown having a dimension of 512 pixels by 512 pixels. As used herein, a pixel is the size of a dot produced by an illumination source as it impinges on an inspection surface. For example, using a laser capable of producing a UV beam having a wavelength of 257 nm, a dot having a 125 nm (0.125 µm) diameter can be used to define a single pixel. Thus, having a dimension of 512 pixels by 512 pixels, the depicted reference block 201 is about 64 µm by 64 µm in size. The inventors contemplate that reference blocks of different shapes and sizes can also be used to practice the invention. Other preferred block sizes include 1024×1024 pixel blocks.

A method embodiment of the present invention uses a plurality of reference blocks to generate a reference "cluster" which is compared with sample blocks to detect the presence of defects in an inspection surface. In order to generate a reference cluster, several defect free reference blocks are scanned to create a suitable reference cluster. Because masks are known to be generally defect-free (for example, defect densities on the order of about 1 part per billion or less are common) it is rather unlikely that any given block will have a defect located therein. Therefore, due to the relative scarcity of defects, the reference blocks can be chosen from virtually any point on the surface to be inspected. Any number of reference blocks can be chosen. However, 6–12 reference blocks are preferred. Choosing more blocks takes longer to construct. And using fewer blocks can increase the likelihood of generating false positive later in the process. Therefore, any number of reference blocks can be used, but a plurality of reference blocks in the range of about 6–12 blocks is preferred.

Using an inspection apparatus (e.g., like the one depicted in FIG. 1), each point (pixel) in a reference block is illuminated. The light intensity values are measured by the detector element for each pixel. Since the values for transmitted light and reflected light are not separated, what is measured is the summed light intensity value of the light received by the photodetector element. The summed light intensity value includes the light transmitted through the inspected surface and the light reflected from the surface for each point (pixel). In addition to detecting the summed light intensity value, the precise location of each measured pixel is also known. Once summed light values are determined for each pixel in a block, these values are mapped onto a coordinate system. The measured light values can include the summed light intensity, or in some cases the measured values can include the transmitted light values of the reflected light values by themselves. Additionally, filtered values for these measured values can be obtained. Examples of such filtering include taking the first derivative or the second derivative of the measured values. Additionally, other filtering functions (e.g., the optical transfer function) can be used to generate filtered values for the measured values.

Figure 3A:
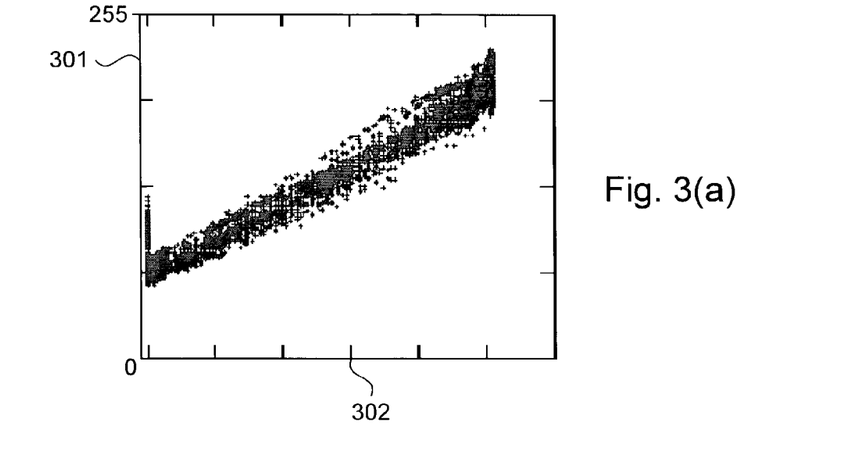
FIGS. 3(a)–3(c) are graphical depictions of reference blocks mapped onto a two-axis coordinate system in accordance with the principles of the present invention.
Figure 3B:
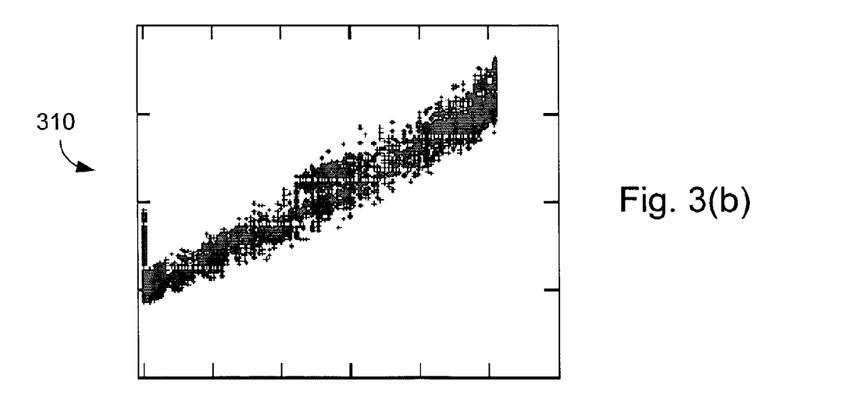
Figure 3C:
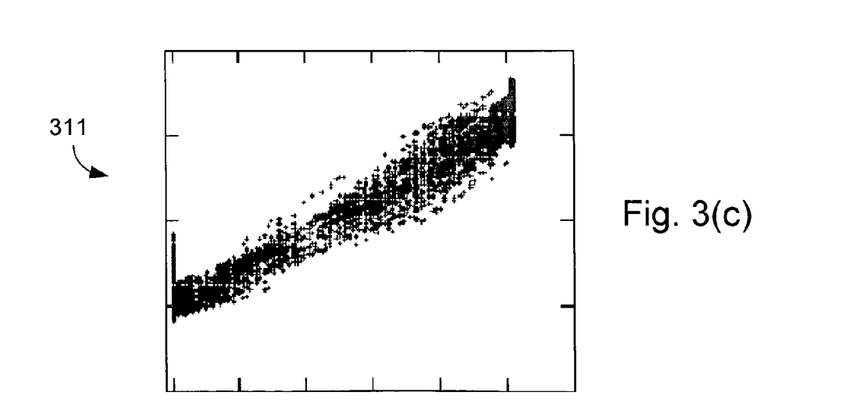

FIGS. 3(a)–3(c) are typical examples of mappings of summed light measurements onto a coordinate system. In these depictions, each pixel is represented by a single black dot. FIG. 3(a) depicts one such mapping of summed light intensity values onto a coordinate system. In this depiction, a 512 pixel by 512 pixel reference block is scanned producing 262,144 data points. Typically, the data points are generated as an electronic signal by the photodetector of the inspection apparatus and output as a reference signal of a certain value. In the depicted embodiment, the first coordinate axis 301 is defined by the summed light intensity value measured for each pixel. In the depicted embodiment, the intensity is measured using an 8-bit scale. Thus, the light intensity ranges from 0 to 255. Such a scale is given as an example and is not intended as limiting. Many other scales and measurement parameters are possible and known to persons of ordinary skill in the art. In the depicted embodiment, a second coordinate axis 302 is defined by calculated database value for each pixel. For most masks, a digitally generated database is used to create the mask. This database is an extremely precise representation of the desired mask. In addition to being able to generate reproductions of the mask, the database can be used, in accordance with the principles of the present invention, to check for defects in the mask. The database is subject to processing to develop a digital model of the optical performance of the database. This model is also referred to as a rendered database. Thus, each reference block on the actual mask has a corresponding reference block stored in the database. This corresponding reference block is rendered using mathematical processing algorithms in order to create a model of the calculated optical performance of a corresponding reference block. This model provides a simulated representation of the optical performance of the corresponding reference block. In one embodiment, this model is used to create calculated values for the summed light performance for the corresponding reference block. These calculated values are sometimes referred to as comparison values. Many mathematical algorithms for modeling optical behavior in this manner are known to those having ordinary skill in the art. For example, the database can be filtered or rendered using the Optical Transfer Function (OTF) of the inspection system.

Figure 4A:
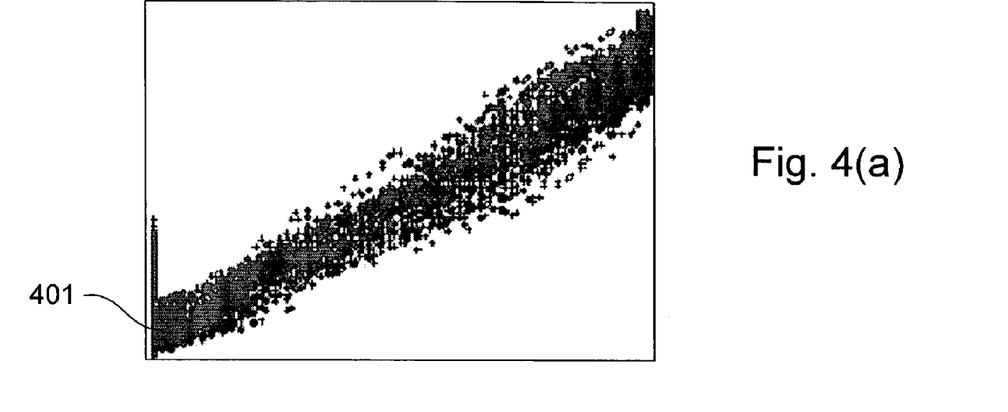
FIG. 4(a) is a graphical depiction of a raw reference cluster in accordance with the principles of the present invention.

Thus, the model can be used to define the second coordinate axis 302 for the coordinate system. For example, each pixel can be mapped to the coordinate system using actual measured summed light values defining one axis 301 and calculated summed light values obtained from the model to define the other axis 302. Thus, a comparison of summed light intensity values to database values can be conducted to search for defects in the mask. FIG. 3(*a*) simulates a depiction of 262,144 pixels (data points from a 512×512 reference block) mapped onto a coordinate system with first axis 301 defined by actual measured summed light intensity values for each pixel and second axis 302 defined by calculated values for summed light intensity for each pixel. In order to generate a reference cluster, a plurality of reference blocks are mapped in this way. FIGS. 3(*b*) and 3(*c*) depict the mapping 310, 311 of additional defect-free reference blocks to a similar coordinate system. In one embodiment, twelve (12) such mappings are generated. These mappings are combined to create an aggregate mapping, also referred to as a raw reference cluster or a raw "slug". One example of such a raw reference cluster is depicted in FIG. 4(*a*). It is to be noted that the shape and size of such raw slugs can vary widely depending on the choice of coordinate axes or nature of the measurements.

Figure 4B:
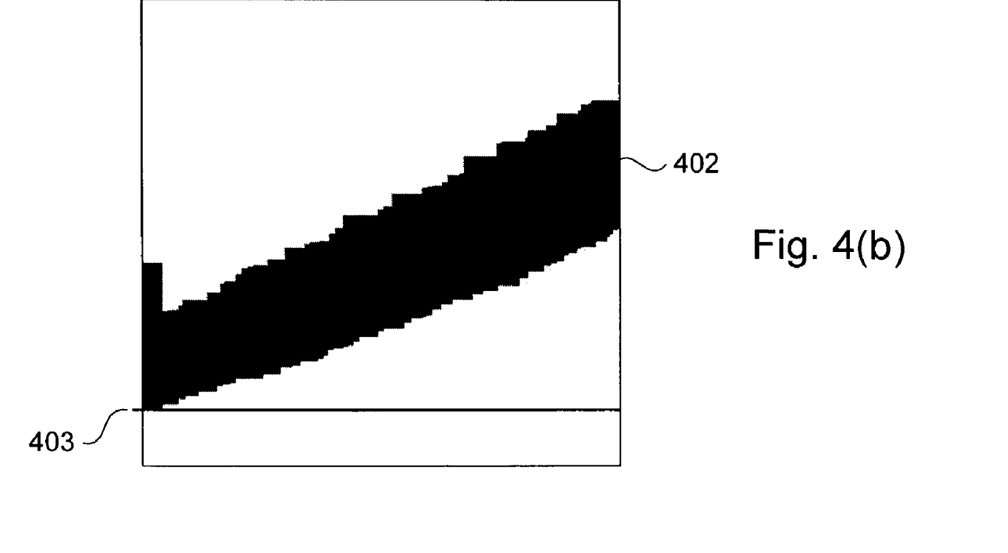
FIG. 4(b) is a graphical depiction of a processed reference cluster in accordance with the principles of the present invention.

Referring to FIG. 4(*b*), once the raw reference cluster is generated it is processed to create a solid reference cluster 402 (or "slug"). Although optional, such processing provides significant advantages and is therefore preferred. Generally, in such processing the extreme outlying pixels are identified and removed and the spaces between the individual pixels are filled in, leaving a solid reference cluster 402. One process suitable for such processing is a dilation process. Many such dilation processes can be used and are known to those having ordinary skill in the art. In one example, a binary dilation process can be used. These and other dilation processes are well known to persons having ordinary skill in the art. Typical examples of suitable dilation processes can be found in many image processing texts. For example, several suitable processes are described in "Algorithms For Image Processing and Computer Vision" (1997) by J. R. Parker, which is hereby incorporated by reference in its entirety. Specific implementations of satisfactory dilation processes can be found at pages 70–110. Also, further implementations and examples can be found in the application libraries of programs such as MATHCAD® distributed by Math Soft of Cambridge, Mass. It should be noted that in one embodiment, a reference cluster can be generated using only the calculated values for summed light as obtained from a database model of the inspection surface.

Upon obtaining the reference cluster, a threshold value can be defined. In one embodiment, the threshold value can simply be defined as a measured light intensity less than the lowest value for the reference cluster 402. This threshold value defines a baseline value. Measured pixels having summed light intensities below the baseline are indicative of a likely defect. FIG. 4(*b*) illustrates such a baseline by the threshold value 403. In one example, using 8-bit data, a value of 40 can be used to define the threshold value 403. The threshold value is independently determined for each mask.

At this point, sample blocks (non-reference blocks) taken from the inspection surface are scanned. The entire mask is scanned, sample block by sample block (e.g., blocks comprising 512 pixels by 512 pixels), until the desired inspection surface is inspected. Each pixel having a measured summed light intensity of less than the threshold value (here, as an example, 40) are classified as potential defects. Because the precise location of each pixel on the inspection surface is known, once these defect pixels are identified, they can be plotted onto a map of the mask surface to determine the location of the defects.

Although the foregoing implementation has the advantage of being very simple, it is not the most preferred implementation. In another more preferred embodiment, the reference cluster can be thought of as a representation of a defect-free area. When individual scanned blocks are compared to the reference cluster, those scanned pixel falling outside the boundaries of the reference cluster are indicative of pixels that correspond to a defect. Like the foregoing process, the entire mask is scanned, block by block (e.g., blocks comprising 512 pixels by 512 pixels), until the desired portions of the inspection surface are inspected. Once scanned, each of the pixels is plotted in a manner similar to that described for the reference blocks. For example, measured summed light values versus calculated summed light values calculated from a database model. In scanned sample blocks without defects, the appearance of the plotted scanned pixels is very similar to that of the reference cluster. In scanned sample blocks containing defects, the scanned pixels that correspond to defects fall outside the boundaries of the reference cluster.

Figure 5:
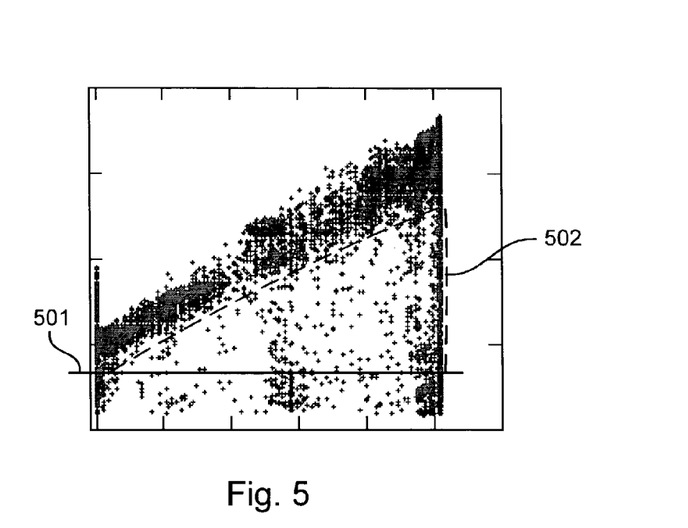
FIG. 5 is a graphical depiction of a sample block having a defect with the block being shown mapped onto the two-axis coordinate system depicted in FIGS. 3(a)–3(c) in accordance with the principles of the present invention.

FIG. 5 depicts the mapped pixels of a scanned sample block having a defect therein. As with the immediately foregoing embodiment, all the pixels having measured summed light intensities less than a threshold value 501 would be classified as defects. In addition, all the pixels falling outside the reference cluster are also classified as defects (e.g., the pixels having a measured summed light intensity value of less than the threshold 501 and the pixels mapped outside the reference cluster, such as those in the region 502). In certain circumstances, pixels that are mapped above the reference cluster can also be classified as defect pixels.

Figure 6:
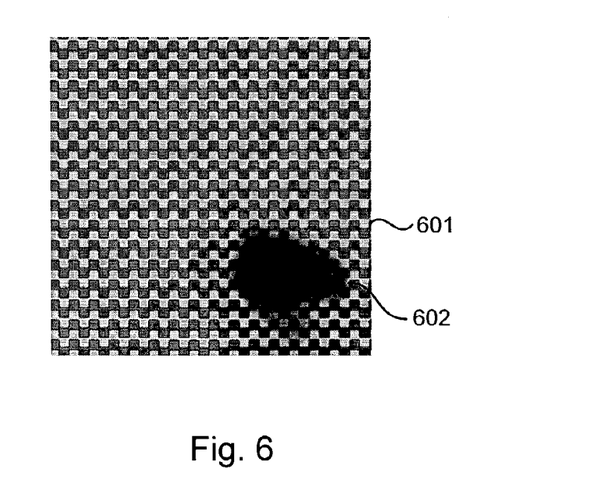
FIG. 6 is a graphical depiction of a sample block showing the size and location of a defect located therein.

FIG. 6 shows another plot of each pixel in FIG. 5. As previously explained, FIG. 5 is a depiction of each pixel in a scanned sample block (in this example, the 512 pixel by 512 pixel sample block mapped to FIG. 5). In FIG. 6, these same pixels are plotted by position and by intensity of summed light. The illustrated embodiment shows the checkerboard test pattern 601 of an example mask surface with a blemish (defect) 602 in the lower right hand corner.

Figure 7:
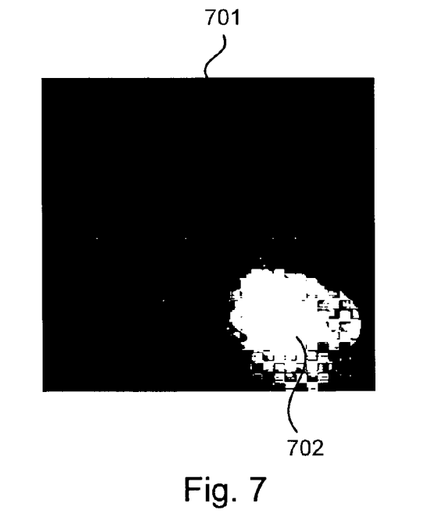
FIG. 7 is a graphical depiction of the defect pixels shown in FIG. 5.

FIG. 7 is a diagram similar to that of FIG. 6, with the exception that only the pixels of FIG. 5 that are classified as defect pixels have been plotted (those in region 502 and below 501). The pixels that lie within the boundaries of the reference cluster of FIG. 5 are not plotted and are depicted only as a black background 701. Thus, the size and location of the defect 702 is clearly evident.

Figure 8A:
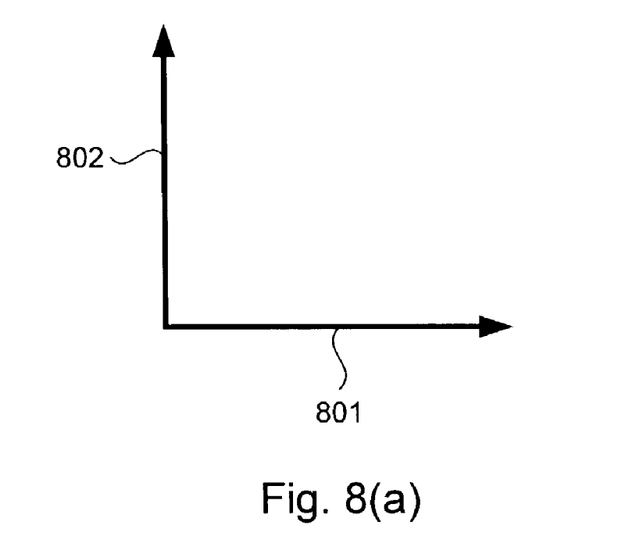
FIG. 8(a) is a depiction of a two-axis coordinate system embodiment used in accordance with the principles of the present invention.

Thus, using the above-described embodiments, by performing a comparison of measured values obtained by scanning the inspection surface mask to calculated values determined from a database, the entire surface of a mask or other surface to be inspected can be inspected for defects. Additionally, the values represented by the coordinate axes of the coordinate system can be modified to examine different aspects of the inspected surface. For example, referring to FIG. 8(*a*), another embodiment defines a first coordinate axis 801 using values derived from the calculated light intensity values obtained from the modeled database. Such derived values are obtained using the calculated values as a starting point. For example, the calculated database value for summed light intensity can be filtered using various mathematical filtering algorithms to obtain the derived value. For example, the first derivative of the calculated database value for summed light intensity can be used as the derived value. This will provide information concerning the rate of change in the modeled database value for summed light intensity. In short, the summed light value for a pixel can be displayed on one axis and the first derivative value of the rendered database can be displayed on another axis. By viewing data in this way it may be possible to detect defects not visible using other approaches. In another example, the second derivative of the calculated database value for summed light intensity can be used one axis and compared to a measured value (for example, transmitted light, reflected light, or summed light) on another axis. As can be appreciated by those having ordinary skill in the art, many other filtering algorithms can be used to modify database and measured values and then compared to detect defects. Persons having ordinary skill in the art are aware of numerous other types of processing that can be used with the calculated database values to generate other values related to the calculated database values. Additionally, the parameters for the second coordinate axis 802 can also be modified. For example, rather than using the actual measured values for summed light intensity, this data can be processed to obtain values related to the actual measured values for summed light intensity. Thus, filtering and other signal processing techniques can be also used to treat the actual measured data before it is mapped.

Another extremely advantageous feature of the invention is that it can detect the presence of defects without the need for database information. Instead, embodiments of the invention can use the summed light measurements from the inspection surface to conduct analysis of the surface. The process is largely the same as described hereinabove. Measurements of summed light are made for a series of reference blocks. The pixels of the reference blocks are mapped to a coordinate system. The difference being that the axes of this coordinate system can be defined by parameters solely derived from the measured summed light intensity values. For example, the pixels can be mapped onto a coordinate system wherein one axis reflects the actual measured values for summed light intensity and another axis is defined by parameters derived from the actual measured values for summed light intensity. In one embodiment, a first axis reflects the actual measured values for summed light intensity and a second axis is defined by filtered values for the measured summed light intensity. In such an example, each pixel is mapped as a function of the measured values for summed light intensity on a first axis versus the first derivative for the measured values for summed light intensity on a second axis. Additionally, the summed light values (or values derived from the summed light values) can be compared to measurements of transmitted light values or reflected light values. In the same manner as described above, such coordinate systems can be used to map reference blocks and generate a reference cluster which is then compared to other scanned sample blocks of the inspection surface to locate defects.

Figure 8B:
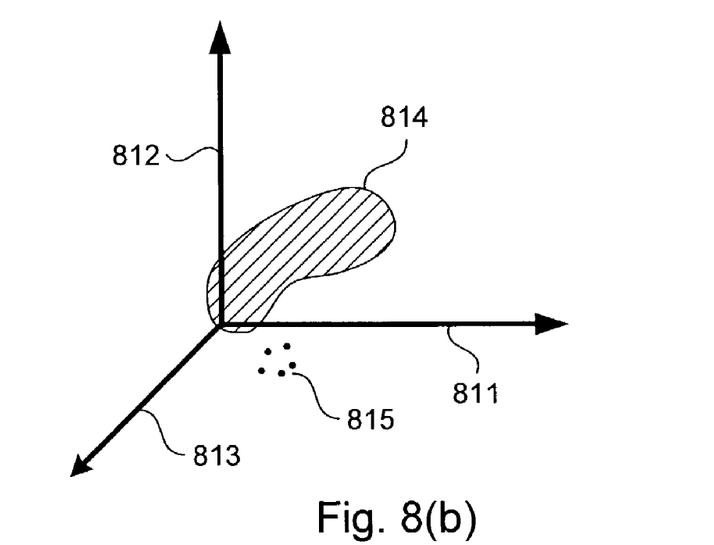
FIG. 8(b) is a depiction of a reference volume on a three-axis coordinate system embodiment in accordance with the principles of the present invention.

In addition to two axis systems, three axis (or more) coordinate systems can be used to enhance the embodiments of the invention. For example, as depicted in the embodiment of FIG. 8(b), a first axis 811 is defined by measured values of summed light, a second axis 812 is defined by the first derivative of measured values of summed light, and a third axis 813 can be defined by calculated values for summed light determined from a database model of the inspection surface. Many possible alternative axes can be used in place of the ones named. Examples include, but are not limited to, transmitted light values, reflected light values, the sum of the transmitted and reflected light values, values calculated from database models etc. In particular, derived values (e.g., values filtered using the first or second derivatives of the measured or calculated values) of the measured or calculated values can be used. Moreover, any of the forgoing values subjected to any of many filtering algorithms known to persons having ordinary skill in the art can be used. Also, if desired, more parameters can be added to generate four or more axis coordinate systems. As previously described, reference blocks are analyzed and the data is mapped to the coordinate system in accordance with the parameters defined by the various axes. In the case of a three-axis coordinate system, the reference blocks are used to generate a three-dimensional reference cluster 814. The three-dimensional reference cluster 814 can be "filled out" using three-dimensional dilation algorithms as are known in the art. Thus, the reference cluster defines a three-dimensional reference volume. Again, the inspection surface can be scanned, sample block by sample block, for the presence of defects. Pixels from the scanned sample blocks are then analyzed. Those pixels falling outside the volume 815 defined by the reference cluster 814 are defined as representative of possible defects in the inspection surface. These defects can then be identified and located. At this point such cleaning, correction, or any other remedial measures can be taken to rectify the defects.

In another embodiment, the inspection surface can be directly compared to the database model on a pixel-by-pixel basis. In general, such an embodiment works as follows. The database is rendered using a suitable model to produce calculated values that can be used as comparison values to predict the intensity of actual summed light produced by each pixel during inspection. Then the inspection surface is inspected pixel-by-pixel. The actual measured values for summed light are compared to the predicted values. If the actual measured value for a pixel is less than the comparison value it is indicative of a possible defect. Tolerances can be set to further enhance the accuracy of this embodiment. For example, if the actual measured value for a pixel is 20% less than the comparison value, then it is likely that the reduction of summed light intensity is due to the presence of a defect. Additionally, the surface can be compared in a patch (1024 pixel×1024 pixel) by patch comparison of the inspected surface.

Figure 9A:
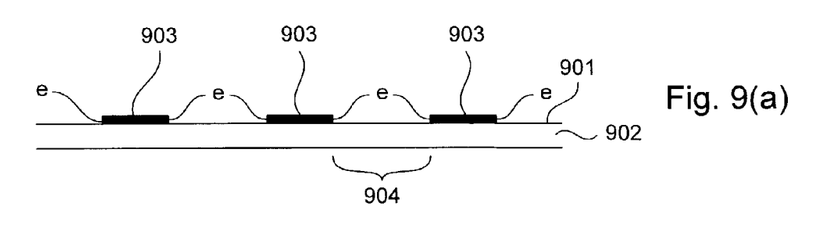
FIG. 9(a) is a cross-sectional view of a portion of one embodiment of a mask surface.

In the following embodiment, another approach is disclosed. FIG. 9(a) is a schematic depiction of an inspection surface 901 and a graph of an electronic signal 911 associated with the inspection surface 901. In one embodiment, the inspection surface 901 is a mask. As depicted here, the inspection surface 901 is a quartz substrate 902. The quartz substrate 902 has formed thereon a pattern 903. Commonly the pattern 903 is formed using opaque or phase shift materials. One common implementation uses a mask pattern formed of chromium. As the inspection surface 901 is illuminated by a pair of coaxial light beams (e.g., a reflected beam and a transmitted beam) passing through each point on the inspection surface 901 a photodetector element collects and measures the sum of the light beams. The illumination source can be set such that the sum of the reflected beam R and the transmitted beam T is equal to a constant C for non-edge regions. This means that if the pair of coaxial light beams impinge on the center of an opaque portion (e.g., 903) the sum of T and R equals C. Similarly, if the pair of coaxial light beams impinge on the center of a quartz (largely transmissive) portion 904 between the opaque regions, the sum of T and R also equals the same constant C. This signal value C can be thought of as the comparison value. The difficulty arises in the edge regions e where diffraction, reflection, and other optical effects reduce the intensity of the summed light to a level below C. These "edge effects" must be compensated for in order to maintain accuracy in defect detection. Similar difficulties must be addressed when phase shift materials are used.

Once the illumination source is set such that the sum of the reflected beam R and the transmitted beam T are equal to a constant C, the inspected surface 901 can be scanned. For purposes of this explanation, the illustrations of FIGS. 9(a)–9(d) refer to a cross section of an inspection surface one pixel wide. This one pixel wide surface is scanned and the resulting signal 911 produced by a photodetector element is graphed in FIG. 9(b). As shown, the signal 911 generally has a summed light intensity value of about the constant C. However, at the edges e the summed light intensity value drops below C forming signal troughs 912. This signal 911 can be used to identify defects in the inspection surface 901.

Figure 9B:
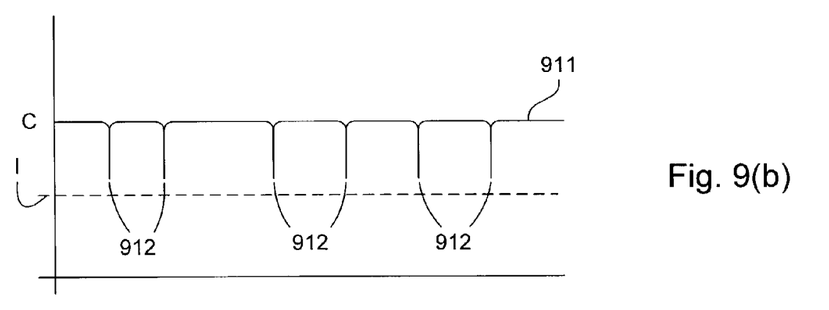
FIGS. 9(b)–9(d) are graphical depictions of electrical signals associated with summed light received from an inspection surface in accordance with the principles of the present invention.

In one implementation, a threshold value I (comparison value) is defined. When the signal 911 drops below the threshold value I it is indicative of the presence of a defect. This threshold value I can be defined, for example, by setting the threshold value I below the minimum signal value for the troughs 912. This threshold value I is shown by the dotted line.

Figure 9C:
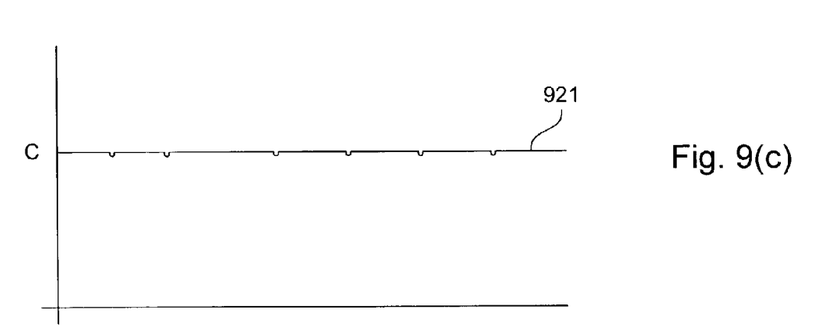

In an alternative embodiment, filtering can be applied to the signal 911 to "smooth" the profile created by the signal. An example of such a profile is shown in FIG. 9(c) which depicts a smoothed signal 921. Such smoothing can be achieved using, for example, cross-correlation routines known and used by those having ordinary skill in the art.

Additionally, edge effects have a variety of consistent characteristics that can be used to distinguish them from defects. For example, edges generally represent contiguous regions with consistent edge profiles (e.g., consistent depth, width, and slope profiles) that permit the edge effects to be compensated for. Also, as is known in the art, Fourier filtering can be used to compensate for the effects of the edges. Moreover, other pattern recognition techniques known to persons having ordinary skill in the art can be used to compensate for the effects of surface patterns to obtain "smooth" signal profiles.

These smoothed signals 921 are more sensitive to the presence of defects than the signal 911 depicted in FIG. 9(b). Additionally, such a signal 921 is less likely to confuse a trough caused by edge effects with a reduced signal caused by the presence of a defect.

Figure 9D:
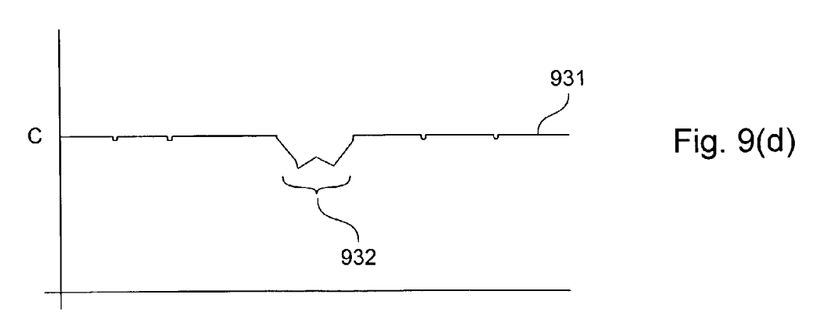

With reference to FIG. 9(d), a signal profile for a defect is shown using a smoothed signal (such as that of FIG. 9(c)). The signal 931 is set at a constant value C. In one example of a defect, an extended deep trough 932 in the signal 931 indicates a defect.

The present invention has been particularly shown and described with respect to certain preferred embodiments and specific features thereof. However, it should be noted that the above-described embodiments are intended to describe the principles of the invention, not limit its scope. Therefore, as is readily apparent to those of ordinary skill in the art, various changes and modifications in form and detail may be made without departing from the spirit and scope of the invention as set forth in the appended claims. Other embodiments and variations to the depicted embodiments will be apparent to those skilled in the art and may be made without departing from the spirit and scope of the invention as defined in the following claims. In particular, it is contemplated by the inventors that embodiments of the invention include coordinate axes defined by measured summed light values, measured transmitted light values, measured reflected light values, calculated summed light values, calculated transmitted light values, calculated reflected light values, filtered measured summed light values, filtered calculated summed light values, values that are related to or derived from calculated summed light values, and values that are related to or derived from measured summed light values, and also values derived from the measured or calculated transmitted or reflected light values. The inventors also contemplate pixel-by-pixel analysis of the inspected surface using summed light measurements. Further, reference in the claims to an element in the singular is not intended to mean "one and only one" unless explicitly stated, but rather, "one or more". Furthermore, the embodiments illustratively disclosed herein can be practiced without any element, which is not specifically disclosed herein.

We claim:

1. A surface inspection method for detecting defects in a substrate, the method comprising:
   generating a reference cluster by measuring summed light intensity values for light reflected by the substrate and for light transmitted through the substrate and mapping the measured summed light intensity values onto a coordinate system wherein mapping the measured summed light intensity values onto a coordinate system comprises mapping the measured summed light intensity values onto a two-axis coordinate system and wherein the reference cluster comprises a two-dimensional reference area, wherein a first axis is defined by at least one of the measured summed light intensity values or values related to the measured summed light intensity values, and a second axis is defined by values derived from a model of substrate optical performance;
   comparing measured summed light intensity values with the reference cluster; and
   determining whether the measured summed light intensity values for the substrate are representative of a defect of the substrate.

2. The surface inspection method of claim 1 wherein a first axis is defined by the measured summed light intensity values.

3. The surface inspection method of claim 1 wherein a first axis is defined by values related to the measured summed light intensity values.

4. A surface inspection method for detecting defects in a substrate, the method comprising:
   generating a reference cluster by measuring summed light intensity values for light reflected by the substrate and for light transmitted through the substrate and then mapping the measured summed light intensity values onto a coordinate system, wherein mapping the measured summed light intensity values onto a coordinate system comprises mapping the measured summed light intensity values onto a two-axis coordinate system wherein a first axis is defined by the measured summed light intensity values and a second axis is defined by a value related to the measured summed light intensity values and obtained by filtering the measured summed light intensity values and wherein the reference cluster comprises a two-dimensional reference area;
   comparing measured summed light intensity values with the generated reference cluster; and
   determining whether the measured summed light intensity values for the substrate are representative of a defect of the substrate.

5. The surface inspection method of claim 4 wherein the filtering is achieved by taking the one of the first derivative of the measured summed light intensity and the second derivative of the measured summed light intensity.

6. A surface inspection method for detecting defects in a substrate, the method comprising:
  generating a reference cluster by measuring summed light intensity values for light reflected by the substrate and for light transmitted through the substrate and then mapping the measured summed light intensity values onto a coordinate system wherein mapping the measured summed light intensity values onto a coordinate system comprises mapping the measured summed light intensity values onto a three-axis coordinate system and wherein the reference cluster is defined by a three-dimensional reference volumes;
  comparing measured summed light intensity values with the generated reference cluster; and
  determining whether the measured summed light intensity values for the substrate are representative of a defect of the substrate.

7. The surface inspection method of claim 6 wherein a first axis is defined by the measured summed light intensity values and a second axis is defined by values related to the measured summed light intensity values and a third axis is defined by values derived from a model of substrate optical performance.

8. The surface inspection method of claim 6 wherein a first axis is defined by a first value related to the measured summed light intensity values and a second axis is defined by a second value related to the measured summed light intensity values and a third axis is defined by values derived from a model of substrate optical performance.

9. A method for inspecting a substrate for the presence of defects, the method comprising:
  illuminating reference blocks of the substrate;
  detecting summed light values for the reference blocks as a reference signal representative of the summed light;
  combining a plurality of said reference signals to generate a reference cluster;
  illuminating a sample portion of the substrate to generate summed sample light that comprises light transmitted through the sample portion and light reflected by the sample portion;
  detecting a sample data signal representative of the summed sample light; and
  determining whether the summed sample light is representative of a defect of the substrate by comparing the summed sample light to the reference cluster.

10. The method of claim 9 wherein said combining the plurality of reference signals to generate a reference cluster includes mapping the signals onto a coordinate system having one axis defined by summed light intensity values and another axis being defined by values derived from a model of substrate optical performance.

11. A surface inspection method for detecting defects in a substrate, the method comprising:
  measuring light intensity values for pixels representative of the substrate surface;
  generating a reference cluster having outer boundaries using calculated light intensity values for pixels representative of the substrate surface and using said measured light intensity values to generate a reference cluster, wherein the calculated light intensity values are determined using a model of substrate optical performance and wherein generating the reference cluster includes mapping the pixels onto a coordinate system having axes representative of calculated light intensity values and representative of the measured light intensity values;
  comparing the measured light intensity values with the reference cluster; and
  determining whether the measured light intensity values fall outside the boundaries of the reference cluster and are thereby representative of a defect.

12. The surface inspection method of claim 11 wherein the calculated light intensity values include one of a calculated transmitted light value, a calculated reflected light value, and a calculated summed light value, a value derived from the calculated transmitted light value, a value derived from the calculated reflected light value, and a value derived from the calculated summed light value; and
  wherein measured light values include one of a measured transmitted light value, a measured reflected light value, and a measured summed light value, a value derived from the measured transmitted light value, a value derived from the measured reflected light value, and a value derived from the filtered measured summed light value.

13. A surface inspection method for detecting defects in a substrate, the method comprising:
  measuring light intensity values for pixels representative of the substrate surface wherein said measuring includes processing the measured light values to obtain values related the measured light values;
  generating a reference cluster having outer boundaries wherein generating the reference cluster includes mapping the pixels values to a coordinate system with a first axis representing the measured light values and a second axis representing the values related the measured light values;
  comparing the measured light intensity values with the reference cluster; and
  determining whether the measured light intensity values fall outside the boundaries of the reference cluster and are thereby representative of a defect.

14. The surface inspection method of claim 13 wherein the first axis is representative of measured summed light values; and
  wherein the second axis is representative of values related to the measured summed light values.

15. The surface inspection method of claim 14 wherein the values related to the measured summed light values comprise filtered values for the measured summed light values.

16. A surface inspection method for detecting defects in a substrate, the method comprising:
  illuminating the substrate with light;
  measuring summed light intensity values for the substrate;
  generating a slug for the substrate wherein generating the slug comprises using data from at least one of a database model of substrate optical performance, the measured summed light intensity values, or data values derived from the database model of substrate optical performance or derived from the measured summed light intensity values;
  comparing the measured summed light intensity values with the slug; and
  identifying defects in the substrate using the comparison of the measured summed light intensity values with the slug.

17. A surface inspection method for detecting defects in a substrate, the method comprising:
  illuminating the substrate with light;
  measuring summed light intensity values for the substrate;
  generating a slug for the substrate wherein the slug is generated using only information obtained from the measured summed light intensity values;

comparing the measured summed light intensity values with the slug; and identifying defects in the substrate using the comparison of the measured summed light intensity values with the slug.

18. The method claim 17 wherein the slug is generated by measuring summed light intensity values for light reflected by the substrate and for light transmitted through the substrate, and mapping the measured summed light intensity values onto a coordinate system having at least two axes with each axis associated with at least one of measured light intensity values and filtered measured light intensity values.

* * * * *